United States Patent [19]

Carini et al.

[11] Patent Number: 5,731,439
[45] Date of Patent: Mar. 24, 1998

[54] PIPERIDINE CONTAINING AMINOBORNIC ACIDS

[75] Inventors: David John Carini, Wilmington; Joseph Cacciola; Celia Dominguez, both of Newark, all of Del.; John Matthew Fevig, New London, Pa.

[73] Assignee: The DuPont Merck Pharmaceutical Company, Wilmington, Del.

[21] Appl. No.: 409,303

[22] Filed: Mar. 24, 1995

[51] Int. Cl.$^6$ .................. C07F 5/02; C07F 5/04; C07F 5/05
[52] U.S. Cl. .................. 546/13; 514/20; 514/18; 514/89
[58] Field of Search .................. 546/13; 514/20, 514/18, 89

[56] References Cited

U.S. PATENT DOCUMENTS

| | | | |
|---|---|---|---|
| 4,499,082 | 2/1985 | Shenvi et al. | 514/2 |
| 4,963,655 | 10/1990 | Kinder et al. | 530/331 |
| 5,187,157 | 2/1993 | Kettner et al. | 514/18 |
| 5,260,307 | 11/1993 | Ackerman et al. | 514/303 |
| 5,442,100 | 8/1995 | Bjorkquist et al. | 562/7 |
| 5,532,232 | 7/1996 | Ackermann et al. | 514/183 |

FOREIGN PATENT DOCUMENTS

| | | |
|---|---|---|
| A33916/93 | 1/1993 | Australia. |
| 601459A2 | 1/1993 | European Pat. Off.. |
| 63-227573 | 3/1987 | Japan. |

*Primary Examiner*—Ralph H. Dean

[57] ABSTRACT

The present invention relates generally to α-aminoboronic acids and corresponding peptide analogs in which the α-carbon is substituted with an optionally functionalized piperidine containing alkyl group. These compounds are useful as inhibitors of trypsin-like serine protease enzymes.

6 Claims, No Drawings

PIPERIDINE CONTAINING AMINOBORNIC ACIDS

FIELD OF THE INVENTION

The present invention relates generally to α-aminoboronic acids and corresponding peptide analogs in which the α-carbon is substituted with an optionally functionalized piperidine containing alkyl group. These compounds are useful as inhibitors of trypsin-like serine protease enzymes.

BACKGROUND OF THE INVENTION

Simple boronic acids are inhibitors of serine proteases. Shenvi, U.S. Pat. No. 4,499,082 (1985) discloses that peptides containing an α-aminoboronic acid with a neutral side chain were more effective inhibitors of serine proteases exceeding inhibitors disclosed earlier by as much as 3 orders of magnitude in potency. The chemistry of α-aminoboronic acids was further expanded to the synthesis of peptide analogs containing boronic acid with positive charged sidechains, boroLysine, boroArginine, boroOrnithine, and isothiouronium analogs (EPA 0 293 881, Dec. 7, 1988). This series of compounds have provided highly effective inhibitors of thrombin and other trypsin-like enzymes. The boroArginine analogs specifically designed as thrombin inhibitors are highly effective in the inhibition of blood coagulation both in vitro and in vivo.

The most effective inhibitor of human thrombin reported to date is the boropeptide acetyl-D-phenylalanyl-prolyl-boro arginine with a $K_i=0.041$ nM (Kettner et al., *J. Biol. Chem.* 265, 18289 (1990)).

Synthetic thrombin inhibitors containing constrained arginine mimics such as (2-naphthylsulfonylglycyl)- 4-amidinophenylalanyl piperidide (see Stuerzebecher, et. al., *Thromb. Res.*, 29, 635–42 (1983)). 1-[2-[5-(dimethylamino)naphth-1-ylsulfonamido]-3-(2-iminohexahydropyrimidin-5-yl)propanoyl]-4-methylpiperidine dihydrochloride (see Ishikawa, JP 88227572), and N-(trans-4-aminomethylcyclohexylcarbonyl)-4-O-(2-picolyl)-L-tyrosine 4-acetanilide dihydrochloride (see Okamoto, et. al., EP 217286) have been disclosed.

European Patent EP 559046 (also Au-A-33916/93) (filed Mar. 1, 1993, J. Ackerman et al.) discloses a compound of structure (9)

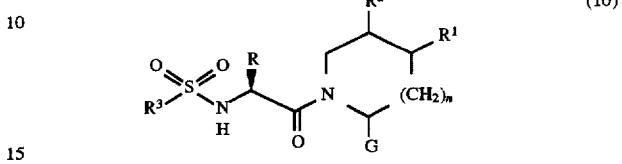

which is useful as a thrombin inhibitor. The substituent definitions are as follows:

X is

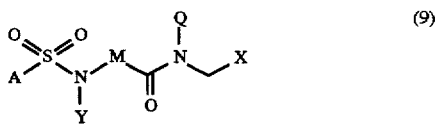

T is $CH_2$ or O. $R^1$, $R^2$, $R^{11}$, and $R^{21}$ are independently H or —$CO_2$— lower alkyl. Y is H, —$CH_2CO_2H$ or —$SO_2$—A'. A and A' are independently aryl, heteroaryl, heterocycle, alkyl, or cycloalkyl. Q is independently H, lower alkyl, or lower-alkyl(OH, $CO_2H$, $CO_2$-lower alkyl). M is —CH(C(O)N(CHR⁴R⁵)R³)CH₂—, —CH(C(O)NHR⁶)CH²—, —CH₂CH (NHC(O)O-benzyl)-, =CH(CH₂)₁₋₂R⁷, =CHCH₂C (O)R⁸, =CHCH₂NH(CO)₁₋₂R⁷, =CHCH₂NHC(O)O-benzyl, or —CH₂CH(NH(CO)₁₋₂R⁷)—.

Eurpoean Patent EP 0601459 (filed Dec. 1, 1993, S. D. Kimball) discloses a compound of the structure (10)

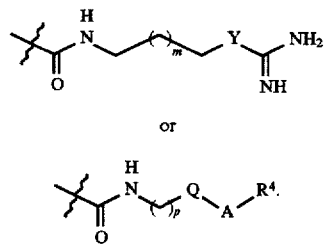

which is useful as a thrombin inhibitor. The substituent definitions are as follows:

G is

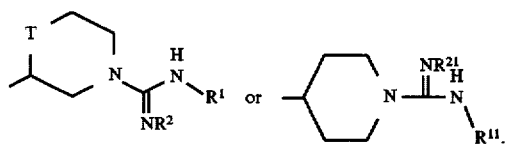

R is H, hydroxyalkyl, aminoalkyl, amidoalkyl, alkyl, cycloalkyl, aryl arylalkyl, alkenyl, alkynyl, arylalkoxylalkyl, or an amino acid side chain. $R^1$ and $R^2$ are independently H, lower alkyl, cycloalkyl, aryl, hydroxy, alkoxy, keto, thioketal, thioalkyl, thioaryl, amino, or alkylaminol. Or together, $R^1$ and $R^2$ are cycloalkyl, aryl or heteroaryl. $R^3$ is lower alkyl aryl, aryl alkyl, heteroaryl, quinolinyl, or tetrahydroquinolinyl. Y is NH or S. Q is a single bond or —C(=O)—. $R^4$ is guanidine, amidine or aminomethyl. A is aryl or cycloalkyl or

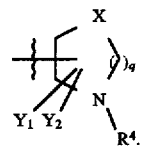

Japanese Patent JP 88227573 (filed Mar. 13, 1987, F. Ishikawa) discloses a compound of the structure (11)

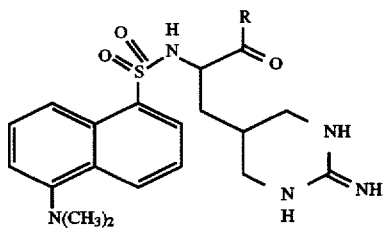

which is useful as a thrombin inhibitor. The substituent definitions are as follows: R is hydroxyl, lower alkoxy, pyrrolidino, or piperidino.

U.S. Pat. No. 5,260,307 (issued Nov. 9, 1993, J. Ackerman et al.) discloses a compound of the structure (12)

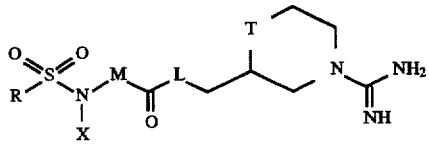
(12)

which is useful as a thrombin inhibitor. The substituent definitions are as follows: R is aryl, heteroaryl or heterocyclyl. T is $CH_2$ or O. L is NH or O. X is H, —$CH_2CO_2H$, —$CH_2CO_2$—$C_{1-4}$alkyl, —$CH_2C(O)$—, (tetra to heptamethyleneimino) or optionally N-mono or N-di-$C_{1-4}$-alkylated —$CH_2C(O)NH_2$. M is R'—$(CH_2)_{1-2}CH$=, R'C(O)$CH_2CH$=, R"C(O)$CH_2CH$=, R'C(O)$_{1-2}$NHCH$_2$CH=, benzyl-OC(O)NHCH$_2$CH=, —$CH_2[R'(CO)_{1-2}NH]CH$—, —$CH_2$(benzyl-OC(O)NH)CH—, or —CH(C(O)—Q)$CH_2$—. Or —N(X)M— is an isoquinolylene or —N(SO$_2$R)—$CH_2$—. R' is aryl, heteroaryl, cycloalkyl or heterocycloalkyl.

Despite the foregoing, more efficacious and specific inhibitors of coagulation proteases are needed as potentially valuable therapeutic agents for the treatment of thrombosis. None of the cited references describe or suggest the new thrombin-inhibiting boronic acid derivatives of the present invention.

The present invention concerns dipeptides which contain an electrophilic derivative of an α-amino acid at $P_1$ (where $P_1$ is the carboxyl terminus of the dipeptide). The $P_1$ substituent contains an optionally functionalized piperidino group, and the $P_1$ is conjugated to an N,N-disubstituted or N-monosubstituted α-amino acid at $P_2$ (where $P_2$ is the end-terminus of the dipeptide). The electrophilic functional groups used to derivatize the $P_1$ amino acid analog are boronic acids and their esters. The N,N-disubstituted α-amino acids are derivatives of an amino acid other than proline where the α-amino group is alkylated and acylated or diacylated to give alicyclic or cyclic substituents.

SUMMARY OF THE INVENTION

The present invention provides novel compounds of formula (I):

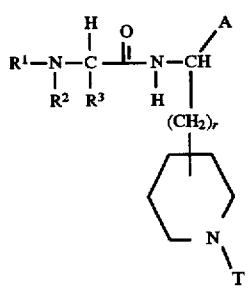
(I)

or a pharmaceutically acceptable salt, hydrate or prodrug thereof, wherein:

$R^1$ is a) —C(=O)—CH[(CH$_2$)$_n$R$^4$]—NR$^5$R$^6$ b) —C(=O)—CR$^8$R$^9$—(CH$_2$)$_p$—R$^4$, c) —C(=O)—CR$^8$R$^9$—W—(CH$_2$)$_r$—R$^4$, d)
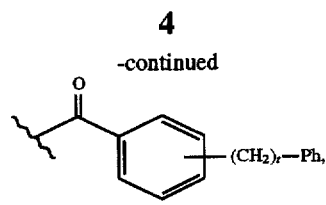

e)
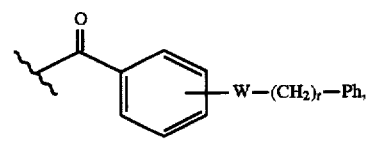

f)
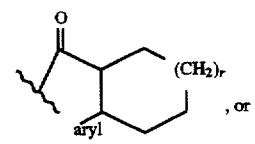

g)
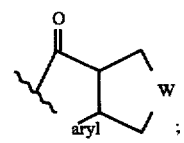

$R^2$ is a) —CH$_2$C(R$^{12}$)$_2$-aryl b) —CH$_2$C(R$^{12}$)$_2$-heteroaryl, c)
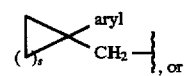

d)
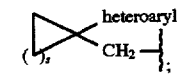

$R^3$ is a) hydrogen, or b) $R^2$ and $R^3$ can be taken together to form:

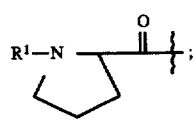

$R^4$ is a) hydrogen, b) $C_1$–$C_4$ alkyl, c) aryl, d) heteroaryl, or e) $C_3$–$C_8$ cycloalkyl;

$R^5$ is a) hydrogen, b) $C_1$–$C_4$ alkyl, or c) —($C_1$–$C_4$ alkyl)-aryl;

$R^6$ is a) —C(=O)—R$^7$, b) —C(=O)—OR$^7$, c) —C(=O)—NR$^5$R$^7$, d) —S(O)$_2$—R$^7$, or e) —S(O)$_2$—NR$^5$R$^7$;

R$^7$ is a) C$_1$–C$_4$ alkyl, or b) —(C$_1$–C$_4$ alkyl)-aryl;

R$^8$ and R$^9$ are independently:

a) hydrogen, b) C$_1$–C$_4$ alkyl, c) aryl, or d) —(C$_1$–C$_4$ alkyl)-aryl;

R$^8$ and R$^9$ call be taken together to form a (C$_3$–C$_7$) cycloalkyl;

R$^{10}$ and R$^{11}$ are independently:

a) hydrogen, b) C$_1$–C$_4$ alkyl, c) —(C$_1$–C$_4$ alkyl)-aryl, d) C$_5$–C$_7$ cycloalkyl, or e) aryl;

R$^{10}$ and R$^{11}$ can be taken together to form:

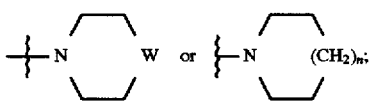

R$^{12}$ is a) —(C$_1$–C$_5$) alkyl, or b) —(C$_1$–C$_5$) fluoroalkyl;

aryl is phenyl or phenyl optionally substituted with from one to three groups selected independently from:

F, Cl, Br, I, C$_1$–C$_4$ alkyl, C$_1$–C$_4$ alkoxy, methylenedioxy, —NO$_2$, —CF$_3$, —S(O)$_r$—(C$_1$–C$_4$ alkyl), CN, —OH, —NH$_2$, —NH(C$_1$–C$_4$ alkyl), —N(C$_1$–C$_4$ alkyl)$_2$, —NHC(=O) (C$_1$–C$_4$ alkyl), —(CH$_2$)$_p$—CO$_2$ (C$_1$–C$_4$ alkyl), or phenyl;

heteroaryl is

2-, 3-, or 4-pyridinyl, 2- or 3-thienyl, 2-, 4-, or 5-pyrimidinyl, 2-, 4-, or 5-oxazolyl, or 2-, 4-, or 5-thiazolyl;

A is a) —BY$^1$Y$^2$, b) —COOR$^5$, c) —CONR$^{10}$R$^{11}$, d) —C(=O)COOR$^5$, or e) —C(=O)CONR$^{10}$R$^{11}$;

T is a) H, b) —C(=NH)NH$_2$, c) —CH(=NH);

W is a) —O—, b) —S(O)$_r$—, c) —NR$^5$—, or d) —NC(=O)R$^7$—;

Y$^1$ and Y$^2$ are a) —OR$^5$, b) —F, c) —NR$^{10}$R$^{11}$, or when taken together Y$^1$ and Y$^2$ form:

d) a cyclic boron ester where said chain or ring contains from 2 to 20 carbon atoms and, optionally, 1–3 heteroatoms which can be N, S, or O, e) a cyclic boron amide where said chain or ring contains from 2 to 20 carbon atoms and, optionally, 1–3 heteroatoms which can be N, S, or O, f) a cyclic boron amide-ester where said chain or ring contains from 2 to 20 carbon atoms and, optionally, 1–3 heteroatoms which can be N, S, or O;

n is 0 or 1;

p is 0 to 3;

r is 0 to 2;

s is 1 to 4; and t is 1 to 3.

[2] Preferred are compounds of formula (I), where:
A is —BY$^1$Y$^2$.

[3] Preferred are compounds of formula (I), where

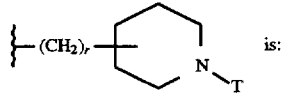

[4] More preferred are compounds of formula (I), where:
A is —BY$^1$Y$^2$ and
where

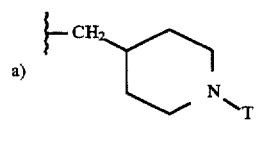

This invention also provides compositions comprising one or more of the foregoing compounds and methods of using such compositions in the treatment of aberrant proteolysis such as thrombosis in mammals or as reagents used as anticoagulants in the processing of blood to plasma for diagnostic and other commercial purposes.

DETAILED DESCRIPTION OF THE INVENTION

As used throughout the specifications, the following abbreviations for amino acid residues or amino acids apply:

Ala=L-alanine
Arg=L-arginine
Asn=L-asparagine
Asp=L-aspartic acid
Aze=azedine-2-carboxlic acid
Cys=L-cysteine
Gln=L-glutamine
Glu=L-glutamic acid
Gly=glycine
His=L-histidine
HomoLys=L-homolysine
Ile=L-isoleucine
Irg=isothiouronium analog of L-Arg
Leu=L-leucine
Lys=L-lysine
Met=L-methionine
Orn=L-ornithine
Phe=L-phenylalanine
Pro=L-proline
Ser=L-serine
Thr=L-threonine
Trp=L-tryptophan
Tyr=L-tyrosine
Val=L-valine
Sar=L-sarcosine
Phe(4-fluoro)=para-fluorophenylalanine The "D" prefix for the foregoing abbreviations indicates the amino acid is in the D-configuration. "D,L" indicates the amino is present in mixture of the D- and the L-configuration. The prefix "boro" indicates amino acid residues where the carboxyl is replaced by a boronic acid or a boronic acid ester. For example, if Q is hydrogen and $Y^1$ and $Y^2$ are OH, the C-terminal residue is abbreviated "boroGly-OH" where "—OH" indicates the boronic acid is in the form of the free acid. The pinanediol boronic acid ester and the pinacol boronic acid ester are abbreviated "—$C_{10}H_{16}$" and "—$C_6H_{12}$", respectively. Examples of other useful diols for esterification with the boronic acids are 1,2-ethanediol, 1,3-propanediol, 1,2-propanediol, 2,3-butanediol, 1,2-diisopropylethanediol, 5,6-decanediol, and 1,2-dicyclohexylethanediol. Compound containing functional groups on Analogs containing sidechain substituents are described by indicating the substituent in parenthesis and/or brackets following the name of the parent residue. For example, the compound where Q is a propyl group substituted, $Y^1$ and $Y^2$ are —OH, and $H^2$ is a 2-aminoimidazol-1-yl group is abbreviated boroGly [($CH_2$)$_3$-(2-aminoimidazol-1-yl)]-OH. Other abbreviations are: Cbz, benzyloxycarbonyl; BSA, benzene sulfonic acid; THF, tetrahydrofuran; Boc-, t-butoxycarbonyl-; Ac—, acetyl; DNA, p-nitro-aniline; DMAP, 4-N,N-dimethylaminopyridine; Tris, Tris(hydroxymethyl) aminomethane; MS, mass spectrometry; FAB/MS, fast atom bombardment mass spectrometry. LRMS($NH_3$—CI) and HRMS($NH_3$—CI) are low and high resolution mass spectrometry, respectively, using $NH_3$ as an ion source.

The following abbreviations are used herein and are defined as follows. The abbreviation "DIBAl" means diisobutylaluminumhydride. The abbreviation "RaNi" means Raney nickel. The abbreviation "LAH" means lithium aluminum hydride. The abbreviation "1,1'-CDI" means 1,1'-carbonyldiimidazole. The abbreviation "Bn" means benzyl. The abbreviation "DMF" means dimethyl formamide. The abbreviation "EtOH" means ethanol.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out. A given reaction may be carried out in one solvent or a mixture of more than one solvent. Depending on the particular reaction step, suitable solvents for a particular reaction step may be selected.

When any variable (for example, $R^{11}$, $R^{12}$, $R^{13}$, m, etc.) occurs more than one time in any substituent or formula for a compound, its definition on each occurrence is independent of its definition at every other occurrence. Thus, for example, if a group is shown to be substituted with 0–3 $R^{11}$, then said group may optionally be substituted with up to three $R^{11}$ meanings and $R^{11}$ at each occurrence is selected independently from the defined list of possible $R^{11}$. Also, combinations of substituents and/or variables are permissible only if such combinations result in stable compounds. By stable compound or stable structure it is meant herein a compound that is sufficiently robust to survive isolation to a useful degree of purity from a reaction mixture. Similarly, by way of example, for the group —C($R^{11}$)$_2$—, each of the two $R^{11}$ substituents on C is independently selected from the defined list of possible $R^{11}$.

When a bond to a substituent is shown to cross the bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. For example, when the substituent is piperidinyl, unless specified otherwise, said piperidinyl group may be bonded to the rest of the compound of a given formula via any atom in said piperidinyl group.

As used herein, "alkyl" is intended to include both branched and straight-chain saturated aliphatic hydrocarbon groups having the specified number of carbon atoms; "fluoroalkyl" is intended to include both branched and straight-chain saturated aliphatic hydrocarbon groups having the specified number of carbon atoms, substituted with 1 or more flurines; "alkoxy" represents an alkyl group of indicated number of carbon atoms attached through an oxygen bridge; "cycloalkyl" is intended to include saturated ring groups, including mono- or bicyclic ring systems, such as cyclopropyl, cyclobutyl, cyclopentyl, cyclohexyl and so forth.

The term "($C_1$-$C_4$ alkyl)aryl" is intended to refer to a $C_1$-$C_4$ alkyl group which is attached through an aryl ring to the residue of the indicated compound.

The term "substituted", as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds of formula (I) wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the compounds of formula (I); phosphate esters, dimethylglycine esters, aminoalkylbenzyl esters, aminoalkyl esters and carboxyalkyl esters of alcohol and phenol functional groups in the compounds of formula (I); and the like.

The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

SYNTHESIS

Compounds of the present invention wherein A is —$BY^1Y^2$ are prepared as shown in Scheme 1. The requisite olefin 1 is hydroborated with catecholborane followed by ester exchange with (+)-pinanediol to provide borane 2. Homologation using the procedure of Matteson et al. (*J. Am. Chem. Soc.* 1983, 105, 2077) affords the α-chloroborane 3. Treatment with lithium hexamethyldisiazide followed by acid furnishes the α-aminoboronic ester 4, which then can be coupled to the desired carboxylic acid employing standard methods for the preparation of peptides. Deprotection affords the piperidines 6, while 6 can be coverted to either to the guanidines 7 or the formamidines 8 employing a variety of reagents known in the literature including those described. Hydrolysis of the boronic esters 6–8, if desired, provides the corresponding boronic acids 9–11.

Scheme 1.

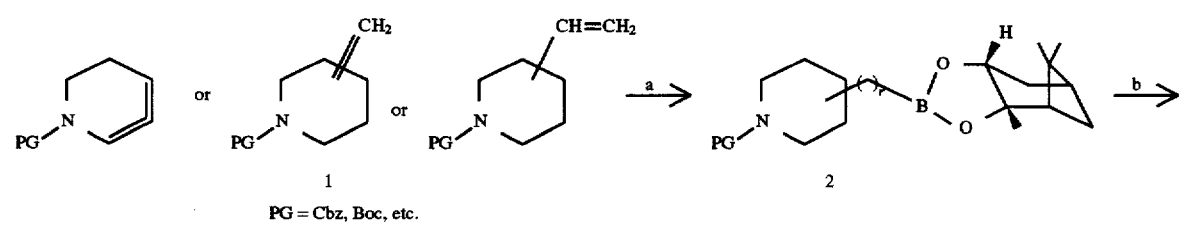

PG = Cbz, Boc, etc.

-continued
Scheme 1.

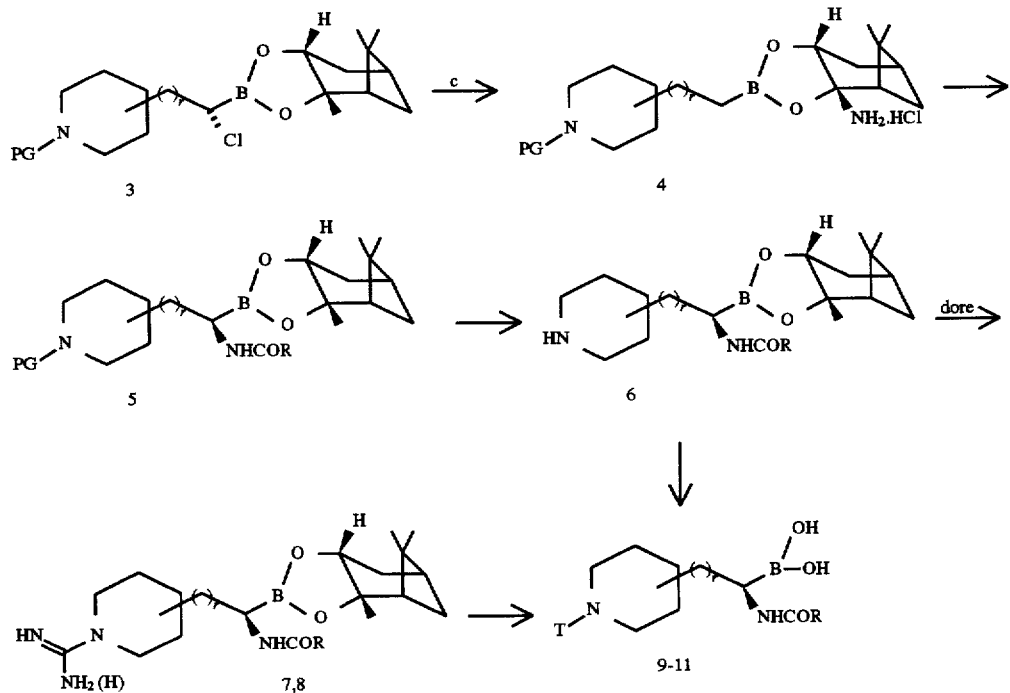

Reagents:  a. catecholborane, then (+)-pinanediol;
b. LiCHCl₂, then ZnCl₂;
c. LiN(TMS)₂, then HCl;
d. formamidinesulfonic acid, 4-DMAP;
e. ethyl formimidate.HCl, 4-DMAP.

Compounds of the present invention wherein A is —COOR⁵ or —CONR¹⁰R¹¹ can be prepared employing procedures described by Schidt et al. (Synthesis 1984, 53; 1992, 487) for the preparation of aminoacids (Scheme 2). Treatment of an appropriate carbonyl compound 12 with phosphonate 13 in the presense of a base such as lithium diisopropyl amide or potassium hexamethyl disilazide affords the acrylate 14. Catalytic hydrogenation utilizing a chiral catalyst such as DuPhos™, followed by deprotection of the amine, provides the aminoacid 15. The synthesis then is completed as previously shown in Scheme 1. At appropriate points in the synthesis a methyl ester intermediate can be readily saponified or converted to an amide by a variety of known methods, thus providing a general route the esters (16), acids (17), and amides (18) of this invention.

Scheme 2.

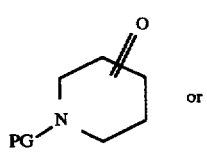

12

-continued
Scheme 2.

[Structures 13, 14, 15, 16–18 shown]

Compounds of the present invention wherein A is —C(=O)COOR⁵ or —C(=O)CONR¹⁰R¹¹ can be prepared as described in Scheme 3 employing the procedure of Angelastro et al. (*J. Org. Chem.* 1989, 54, 3913). Thus the acid 19, prepared as described in Scheme 2, is activated by one of a variety of methods including treatment with base followed isobutyl chloroformate. This active ester then is allowed to react with N,O-dimethylhydroxylamine to afforded the amide 20. Treatment of 20 with the lithium salt of a vinyl ether provides 21 which upon ozonolysis furnishes the α-ketoester 22. Saponification of 22 with aqueous hydroxide provides the α-keoacid 23. The α-ketoamides can be prepared by the procedure of Li et al. (*J. Med. Chem.* 1993, 36, 3472). According to this procedure 22 is protected as the 1,3-dithiolane 24. Finally, treatment of this intermediate with an amine provides 25.

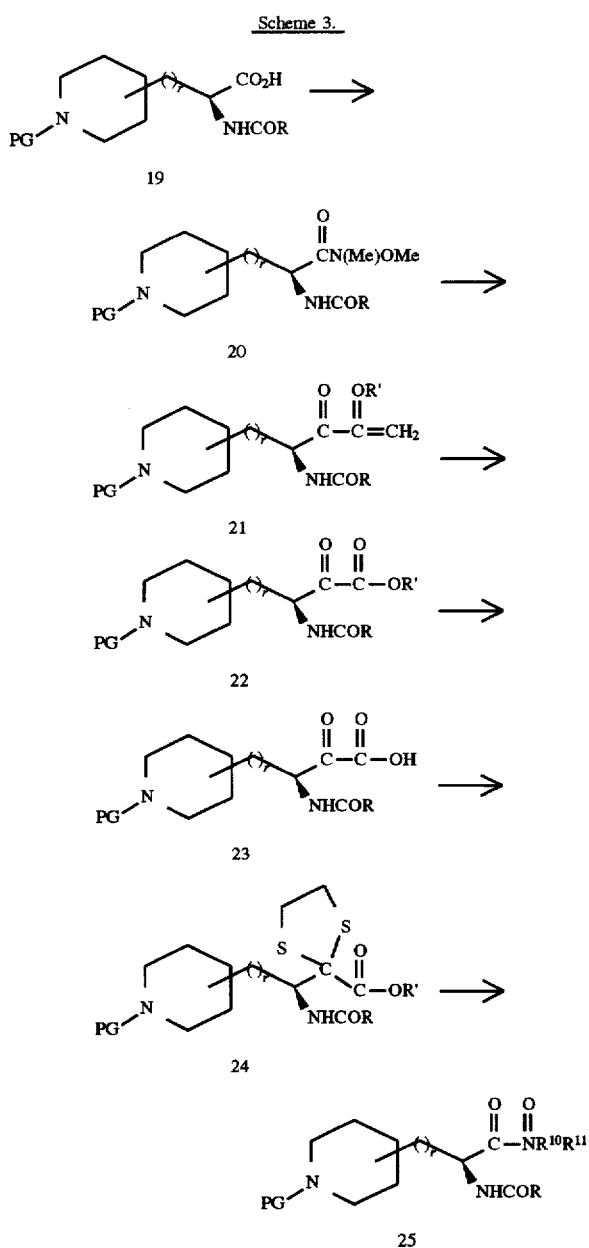

EXAMPLE 1

Synthesis of Acetyl-(D)-Phe-Pro-boroGly-[(1-formamidino-piperidin-4-yl)methyl]-OH hydrochloride.

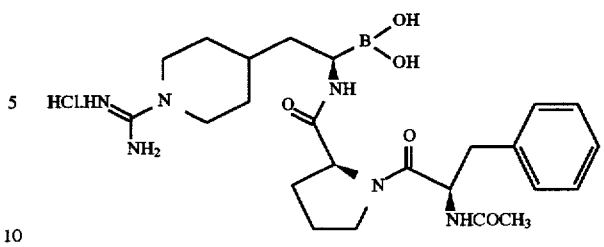

Part A. To 1-benzyloxycarbonyl-4-methylenepiperidine (28.0 g, 120 mmol), prepared as described by De Amici, et al. *Eur. J. Med. Chem.* 1991, 26, 625, at 20° C. was added catecholborane (13.0 mL, 120 mmol), and the mixture was heated to 100° C. for 4 hours. (Caution: an exotherm results upon initiation of the reaction.) After cooling the reaction mixture was diluted with 50 mL of THF, and solution was transferred to a solution of (+)-pinanediol (21.3 g, 125 mmol) in 50 mL of THF at 0° C. The resulting mixture was stirred at 20° C. for 14 hours, and then the solvent was removed under vacuum. The residue was dissolved in hexane, and the solution was stirred briefly with a solution of sodium carbonate (6.50 g, 60 mmol) in water. The organic phase then was washed with saturated aqueous sodium bicarbonate, water, and brine, dried over anhydrous sodium sulfate, filtered, and concentrated. Column chromatography on silica gel (elution: 0–25% ethyl acetate/hexane) afforded 44.6 g (89%) of product. MS: 412 (M+H)$^+$.

Part B. To a solution of methylene chloride (6.86 mL, 107 mmol) in 100 mL of THF at –100° C. was added dropwise n-butyl lithium (2.0M in hexane, 51.4 mL, 103 mmol) at –100° C. To this mixture then was added a solution of the product from Part A (35.2 g, 86 mmol) in 100 mL of THF at –100° C. Finally, a solution of zinc chloride (0.5 M in THF, 257 mL, 128 mmol) at –78° C. was added, and the reaction mixture was allowed to warm slowly to 20° C. and to stir for 16 hours. The resulting solution was diluted with hexane and then was washed with 1.0N hydrochloric acid, water, saturated aqueous sodium bicarbonate, and brine. The solution next was dried over anhydrous magnesium sulfate, filtered, and concentrated. Column chromatography on silica gel (elution: 2–10% ethyl acetate / hexane) provided 32.5 g (83%) of product. MS: 460 (M+H)$^+$.

Part C. To a solution of the product from Part C (27.3 g, 59 mmol) in 180 mL of THF at –78° C. was added lithium hexamethyldisilazide (1.0M in hexane, 59 mL, 59 mmol) dropwise such that the reaction temperature remained at <–70° C. Following the addition the mixture was allowed to warm slowly to 20° C. and was stirred at 20° C. for 14 hours. The solvent was removed under vacuum, and the residue was dissolved in hexane. The resulting suspension was filtered washing with hexane. The total volume of hexane employed was 480 mL. To the filtrate at 0° C. was added dropwise hydrogen chloride (4.0N in 1,4-dioxane, 45 mL, 180 mmol), and the mixture was allowed to warm to 20° C. and stir for 14 hours. Sufficient 1,4-dioxane was added to produce a clear solution (~400 mL) and an additional 15 mL (60 mmol) of 4.0 N hydrogen chloride in 1,4-dioxane was added. The mixture was stirred for 1 hour at 20° C., and then the solvent was removed under vacuum. The residue was dissolved in chloroform. The resulting suspension was filtered, and the filtrate concentrated. Size-exclusion chromatography on Sephedex® LH-20 (elution: methanol) furnished 22.3 g (79%) of product. MS: 441 (M+H)$^+$ for the free-base. Part D. To a suspension of acetyl-(D)-PhePro-OH (2.16 g, 7.1 mmol) in 20 mL of methylene chloride at 20° C. was added N-methylmorpholine (1.56 mL, 14.2 mmol). The mixture was stirred until all solids had dissolved, and then the solution was cooled to −78° C. To this solution was added dropwise isobutyl chloroformate (0.92 mL, 7.1 mmol), and the solution then was stirred at −78° C. for 0.5 hours. To the reaction mixture was added a solution of product C (3.39 g, 7.1 mmol) in 20 mL of methylene chloride, pre-cooled to −78° C. The resulting mixture was stirred at −78° C. for 1 hour, allowed to warm slowly to 20° C., and then stirred for 18 hours at 20° C. The resulting suspension was filtered, and the filtrate was concentrated under vacuum. The residue was dissolved in ethyl acetate, and the solution was washed in order with 0.1N hydrochloric acid, water, saturated aqueous sodium bicarbonate, water, and brine. The solution then was dried over anhydrous sodium sulfate, filtered, and concentrated. Column chromatography on florisil® (elution: 1–5% methanol/chloroform) afforded 3.20 g (62%) of product. MS: 727 (M+H)$^+$.

Part E. A mixture of the product from Part D (3.10 g, 4.3 mmol), palladium on carbon (0.47 g), 4.5 mL of 1.0N hydrochloric acid, and 60 mL of methanol was stirred at 20° C. under hydrogen (1 atm.) for 3 hours. The suspension was filtered through celite®, and the filtrate was concentrated under vacuum. The residue was dissolved in water, and the aqueous solution was washed with diethyl ether and then concentrated under vacuum. The residue was dissolved in chloroform, and the resulting solution was dried over anhydrous sodium sulfate and then concentrated to provide 2.60 g (97%) of product. MS: 593 (M+H)$^+$ for the free-base.

Part F. A mixture of the product from Part E (2.54 g, 4.0 mmol), formamidinesulfonic acid (1.00 g, 8.0 mmol), 4-(dimethylamino)pyridine (0.99 g, 8.0 mmol), and 40 mL of ethanol was refluxed for 14 hours. At this point additional formamidinesulfonic acid (1.00 g, 8.0 mmol) and 4-(dimethylamino)pyridine (0.99 g, 8.0 mmol) was added, and the mixture was refluxed for an additional 8 hours. After cooling, the mixture was filtered, and the filtrate was concentrated under vacuum. The residue was dissolved in chloroform. The resulting solution was washed twice with ice-cold 0.1N hydrochloric acid, twice with ice-cold water, and then with brine. Finally the solution was dried over anhydrous sodium sulfate, filtered, and concentrated. Size-exclusion chromatography on Sephedex® LH-20 (elution: methanol) furnished 1.85 g (68%) of product. MS: 635 (M+H)$^+$ for the free-base.

Part G. A two-phase mixture of the product from Part F (0.94 g, 1.40 mmol), phenylboronic acid (0.85 g, 7.00 mmol), 30 mL of diethyl ether, and 30 mL of water was stirred vigorously at 20° C. for 5 hours. The phases were separated, and the aqueous phase was washed repeatedly with diethyl ether until no phenylboronic acid was detected in the washing by TLC. The aqueous phase was concentrated under vacuum to furnish 0.63 g (84%) of acetyl-(D)-Phe-Pro-boroGly-[(1-formamidinopiperidin-4-yl)methyl]-OH hydrochloride; HRMS: (M+H)$^+$ for $C_{26}H_{39}BN_6O_5$ (ethylene glycol ester of the free-base) calc. 527.315324, found 527.313826.

The examples shown in Table 1, can be prepared by the schemes and procedures above using the appropriate starting materials. These examples are only meant to be illustrative of and are not to be construed as limiting the scope of the present invention.

TABLE 1

| EX | | LRMS Method | Calc | Found |
|---|---|---|---|---|
| 1 | Ac-(D)-Phe-Pro-boroGly-[CH$_2$(1-formamidino-piperidin-4-yl)]-OH | ESI (M + H)$^+$ | 501 | 501 |
| 2 | Ms-(D)-Phe-Pro-boroGly-[CH$_2$(1-formamidino-piperidin-4-yl)]-OH | ESI (M + H)$^+$ | 537 | 537 |
| 3 | Ac-(D)-Phe-Pro-boroGly-[CH$_2$(piperidin-4-yl)]-OH | ESI (M + H)$^+$ | 459 | 459 |
| 4 | Ms-(D)-Phe-Pro-boroGly-[CH$_2$(piperidin-4-yl)]-OH | ESI (M + H)$^+$ | 495 | 495 |
| 5 | Ac-(D)-Phe-Pro-boroGly-[CH$_2$(1-formamidino-piperidin-3-yl)]-OH, diastereomer 1 | ESI (M + H)$^+$ | 501 | 501 |
| 6 | Ac-(D)-Phe-Pro-boroGly-[CH$_2$(1-formamidino-piperidin-3-yl)]-OH, diastereomer 2 | ESI (M + H)$^+$ | 501 | 501 |
| 7 | Ac-(D)-Phe-Pro-boroGly-[CH$_2$(piperidin-3-yl)]-OH, diastereomer 1 | ESI (M + H)$^+$ | 459 | 459 |
| 8 | Ac-(D)-Phe-Pro-boroGly-[CH$_2$(piperidin-3-yl)]-OH, diastereomer 2 | ESI (M + H)$^+$ | 459 | 459 |
| 9 | Ac-(D)-Phe-Pro-boroGly[CH$_2$(1-formiminopiperidin-3-yl)]-C$_{10}$H$_{16}$ | ESI (M + H)$^+$ | 620 | 620 |
| 10 | Ms-(D)-Phe-Pro-boroGly [CH$_2$(piperidin-3-yl)]-OH, diastereomer 1 | ESI (M + H)$^+$ | 495 | 495 |
| 11 | Ms-(D)-Phe-Pro-boroGly[CH$_2$(piperidin-3-yl)]-OH, diastereomer 2 | ESI (M + H)$^+$ | 495 | 495 |
| 12 | CH$_3$(CH$_2$)$_3$SO$_2$-(D)-Phe-Pro-boroGly [CH$_2$(piperidin-4-yl)]-OH | ESI (M + H)$^+$ | 537 | 537 |
| 13 | CH$_3$(CH$_2$)$_7$SO$_2$-(D)-Phe-Pro-boroGly[CH$_2$(piperidin-4-yl)]-OH | ESI (M + H)$^+$ | 593 | 593 |
| 14 | CH$_3$(CH$_2$)$_5$SO$_2$-(D)-Phe-Pro-boroGly[CH$_2$(piperidin-3-yl)]-OH, diastereomer 1 | ESI (M + H)$^+$ | 537 | 537 |
| 15 | CH$_3$(CH$_2$)$_5$SO$_2$-(D)-Phe-Pro-boroGly[CH$_2$(piperidin-3-yl)]-OH, diastereomer 2 | ESI (M + H)$^+$ | 537 | 537 |
| 16 | CH$_3$(CH$_2$)$_7$SO$_2$-(D)-Phe-Pro-boroGly [CH$_2$(piperidin-3-yl)]-OH, diastereomer 1 | ESI (M + H)$^+$ | 593 | 593 |
| 17 | CH$_3$(CH$_2$)$_7$SO$_2$-(D)-Phe-Pro-boroGly[CH$_2$(piperidin-3-yl)]-OH, diastereomer 2 | ESI (M + H)$^+$ | 593 | 593 |
| 18 | N-[3-(3,4-Dimethoxyphenyl)propanoyl]-N-(2,2-dimethyl-2-phenylethyl)Gly-boroGly[CH$_2$(piperidin-4-yl)]-OH | ESI (M + H)$^+$ | 554 | 554 |

Further illustrative of the scope of the present invention are the following compounds in Table 2 which may also be prepared according to the procedures and schemes above.

TABLE 2

19  Ac-(D)-Phe—Pro-boroGly(1-formamidinopiperidin-4-yl)-OH
20  Ac-(D)-Phe—Pro-boroGly[(CH$_2$)$_2$(piperidin-2-yl)]-OH
21  Ac-(D)-Phe—Pro-boroGly[(CH$_2$)$_2$(piperidin-2-yl)]-OH
22  CH$_3$(CH$_2$)$_5$SO$_2$-(D)-Phe—Pro-boroGly[CH$_2$(piperidin-4-yl)]-OH
23  CH$_3$(CH$_2$)$_3$SO$_2$-(D)-Phe—Pro-boroGly[CH$_2$(piperidin-3-yl)]-OH
24  Hydrocinnamoyl-Pro-boroGly[CH$_2$(1-formamidino-

TABLE 2-continued piperidinyl-4-)]-OH
25 Ac-(D)-Phe—Pro-boroGly[CH$_2$(1-formamidino-
    piperidinyl-4-yl)]-C$_{10}$H$_{16}$
26 Ms-(D)-Phe—ProGly[CH$_2$(piperidin-3-yl)]-OH
27 Ms-(D)-PheProGly[CH$_2$(piperidin-4-yl)]-N(CH$_3$)$_2$
28 Ac-(D)-Phe—ProNHCH[CH$_2$(piperidin-3-yl)]-C(=O)COOH
29 Ac-(D)-Phe—ProNHCH[CH$_2$(1-formamidinopiperidin-4-
    yl)]-C(=O)CON(CH$_3$)$_2$
30 N-[3-(3,4-Dimethoxyphenyl)propanoyl]-N-(2,2-
    dimethyl-2-phenylethyl)Gly-boroGly[CH$_2$(piperidin-
    3-yl)]-OH
31 N-(3-phenylpropanoyl)-N-(2,2-dimethyl-2-
    phenylethyl)Gly-boroGly[CH$_2$(piperidin-3-yl)]-OH
32 N-[3-(3,4-Dimethoxyphenyl)propanoyl]-N-(2,2-
    dimethyl-2-phenylethyl)Gly-boroGly[CH$_2$(1-
    formamidinopiperidin-3-yl)]-OH
33 N-[3-(3,4-Dimethoxyphenyl)propanoyl]-N-(2,2-
    dimethyl-2-phenylethyl)Gly-boroGly[CH$_2$(1-
    formiminopiperidin-3-yl)]-OH

UTILITY

The compounds which are described in the present invention represent a novel class of potent, reversible inhibitors of trypsin-like enzymes. Trypsin-like enzymes are a group of proteases which hydrolyzed peptide bonds at basic residues liberating either a C-terminal arginyl or lysyl residue. Among these are enzymes of the blood coagulation and fibrinolytic system required for hemostasis. They are Factors II, X, VII, IX, XII, kallikrein, tissue plasminogen activators, urokinase-like plasminogen activator, and plasmin. Enzymes of the complement system, acrosin (required for fertilization), pancreatic trypsin are also in this group. Elevated levels of proteolysis by these proteases can result in disease states. For example, consumptive coagulopathy, a condition marked by a decrease in the blood levels of enzymes of both the coagulation system, the fibrinolytic system and accompanying protease inhibitors is often fatal. Intervention by a synthetic inhibitor would clearly be valuable. More specifically, proteolysis by thrombin is required for blood clotting. Inhibition of thrombin results in an effective inhibitor of blood clotting. The importance of an effective inhibitor of thrombin is underscored by the observation that conventional anticoagulants such as heparin (and its complex with the protein inhibitor, antithrombin III) are ineffective in blocking arterial thrombosis associated with myocardial infarctions and other clotting disorders. However, a low molecular weight thrombin inhibitor, containing a different functionality, was effective in blocking arterial thrombosis (Hanson and Harker, *Proc. Natl. Acad. Sci. U.S.A.* 85, 3184 (1988). Therefore, we have chosen to demonstrate utility of compounds in the inhibition of thrombin, both as in buffered solutions and in plasma. Specifically, the compounds have utility as drugs for the treatment of diseases arising from elevated thrombin activity such as myocardial infarction, and as reagents used as anticoagulants in the processing of blood to plasma for diagnostic and other commercial purposes.

Compounds of the present invention are expected to be effective in the control of aberrant proteolysis and a number of accompanying disease states such as inflammation, pancretitis, and heritary angioedema.

Compounds of the present invention were shown to be direct acting inhibitors of the serine protease thrombin by their ability to inhibit the cleavage of small molecule substrates by thrombin in a purified system. The direct interaction of representative examples of the compounds of the present invention with human α-thrombin was demonstrated by x-ray crystallographic analysis of the compounds in complex with human α-thrombin. X-ray diffraction patterns were solved for three dimensional structure and showed that these compounds directly interact with the proteolytic active site of human α-thrombin and that the boronic acid portion of the compounds is in close proximity to the serine which is part of the catalytic triad.

The effectiveness of compounds of the present invention as inhibitors of blood coagulation proteases was determined using purified human proteases and synthetic substrates following procedures similar to those described in Kettner et al. (1990).

For these assays, the rate of enzymatic (thrombin, Factor Xa, and Factor VIIa) hydrolysis of chromogenic substrates (S2238 (H-D-Phe-Pip-Arg-pNA), S2222, and S2288, respectively; Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Thrombin and Xa determinations were made in 0.10M sodium phosphate buffer, pH 7.5, containing 0.20M NaCl, and 0.5% PEG 8000. VIIa determinations were made in 0.05M tris buffer, pH 7.6, containing 0.10M NaCl, 4 mM CaCl$_2$, and 0.1% bovine serum albumin. The Michaelis constant, $K_m$, for substrate hydrolysis was determined at 25° C. using the method of Lineweaver and Burk.

Values of $K_i$ were determined by allowing 0.2–0.5 nM human thrombin or human factor Xa (Enzyme Research Laboratories, South Bend, Ind.), or 50 nM human factor VIIa (BiosPacific, Emeryville, Calif.) react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values.

$$\frac{v_o - v_s}{v_s} = \frac{I}{K_i(1 + S/K_m)}$$

where:

$v_o$ is the velocity of the control in the absence of inhibitor;

$v_s$ is the velocity in the presence of inhibitor;

I is the concentration of inhibitor;

$K_i$ is the dissociation constant of the enzyme: inhibitor complex;

S is the concentration of substrate;

$K_m$ is the Michaelis constant.

Using the methodology described above, representative compounds of this invention were evaluated and found to exhibit a $K_i$ of less 20 nM thereby confirming the utility of compounds of the invention as effective inhibitors of human blood coagulation proteases.

These compounds are also useful as anticoagulants for the processing of blood for therapeutic or diagnostic purposes or for the production of blood products or fragments, since contact of blood with the surfaces commonly used for blood collection and storage causes activation of coagulation leading to thrombin formation and clot formation.

Generally, these compounds may be administered orally, parenterally or intravenously to a host to obtain an anti-thrombogenic effect. The dosage of the active compound depends on the mammalian species, body weight, age, and mode of administration as determined by one skilled in the art. In the case of large mammals such as humans, the compounds may be administered alone or in combination with pharmaceutical carriers or diluents at a dose of from 0.02 to 15 mg/kg to obtain the anti-thrombogenic effect, and may be given as a single dose or in divided doses or as a sustained release formulation.

Pharmaceutical carriers or diluents are well known and include sugars, starches and water, which may be used to make tablets, capsules, injectable solutions or the like which can serve as suitable dosage forms for administration of the compounds of this invention. *Remington's Pharmaceutical Sciences*, A. Osol, is a standard reference text which discloses suitable pharmaceutical carriers and dosage forms. The disclosure of this text is hereby incorporated by reference for a more complete teaching of suitable dosage forms for administration of the compounds of this invention.

What is claimed is:

1. A compound of the formula (I)

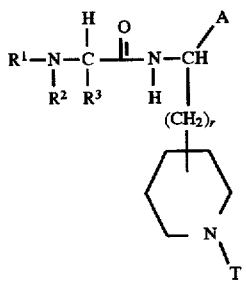
(I)

or a pharmaceutically acceptable salt, wherein:

$R^1$ is
a) $-C(=O)-CH[(CH_2)_rR^4]-NR^5R^6$,
b) $-C(=O)-CR^8R^9-(CH_2)_p-R^4$,
c) $-C(=O)-CR^8R^9-W-(CH_2)_r-R^4$, d) 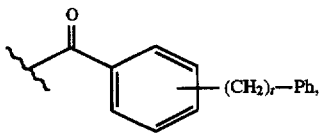

e) 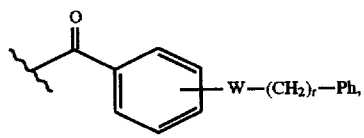

f) 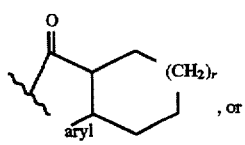, or g) 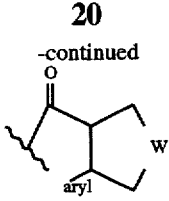;

$R^2$ is
a) $-CH_2C(R^{12})_2$-aryl,
b) $-CH_2C(R^{12})_2$-heteroaryl, c) 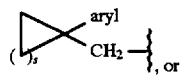, or d) 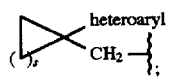;

$R^3$ is
a) hydrogen, or
b) $R^2$ and $R^3$ can be taken together to form:

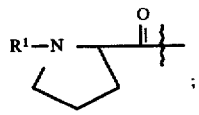;

$R^4$ is
a) hydrogen,
b) $C_1-C_4$ alkyl,
c) aryl,
d) heteroaryl, or
e) $C_3-C_8$ cycloalkyl;

$R^5$ is
a) hydrogen,
b) $C_1-C_4$ alkyl, or
c) $-(C_1-C_4$ alkyl)-aryl;

$R^6$ is
a) $-C(=O)-R^7$,
b) $-C(=O)-OR^7$,
c) $-C(=O)-NR^5R^7$,
d) $-S(O)_2-R^7$, or
e) $-S(O)_2-NR^5R^7$;

$R^7$ is
a) $C_1-C_4$ alkyl, or
b) $-(C_1-C_4$ alkyl)-aryl;

$R^8$ and $R^9$ are independently:
a) hydrogen,
b) $C_1-C_4$ alkyl,
c) aryl, or
d) $-(C_1-C_4$ alkyl)-aryl;

$R^8$ and $R^9$ can be taken together to form a $(C_3-C_7)$ cycloalkyl;

$R^{10}$ and $R^{11}$ are independently:
a) hydrogen,
b) $C_1-C_4$ alkyl,
c) $-(C_1-C_4$ alkyl)-aryl,
d) $C_5-C_7$ cycloalkyl, or
e) aryl;

$R^{10}$ and $R^{11}$ can be taken together to form:

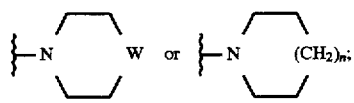

$R^{12}$ is
 a) —($C_1$–$C_5$) alkyl, or
 b) —($C_1$–$C_5$) fluoroalkyl;
aryl is phenyl or phenyl optionally substituted with from one to three groups selected independently from:
 F, Cl, Br, I, $C_1$–$C_4$ alkyl, $C_1$–$C_4$ alkoxy, methylenedioxy, —$NO_2$, —$CF_3$, —$S(O)_r$—($C_1$–$C_4$ alkyl), CN, —OH, —$NH_2$, —NH($C_1$–$C_4$ alkyl), —N($C_1$–$C_4$ alkyl)$_2$, —NHC(=O)($C_1$–$C_4$ alkyl), —($CH_2$)$_p$—$CO_2$($CFC_4$ alkyl), or phenyl;
heteroaryl is
 2-, 3-, or 4-pyridinyl, 2- or 3-thienyl, 2-, 4-, or S-pyrimidinyl, 2-, 4-, or 5-oxazolyl, or 2-, 4-, or 5-thiazolyl;
A is —$BY^1Y^2$;
T is
 a) H,
 b) —C(=NH) $NH_2$,
 c) —CH(=NH);
W is
 a) —O—,
 b) —$S(O)_r$—,
 c) —$NR^5$—, or
 d) —NC(=O)$R^7$—;
$Y^1$ and $Y^2$ are
 a) —$OR^5$,
 b) —F,
 c) —$NR^{10}R^{11}$, or
when taken together $Y^1$ and $Y^2$ form:
 d) a cyclic boron ester where said chain or ring contains from 2 to 20 carbon atoms and, optionally, 1–3 heteroatoms which can be N, S, or O,
 e) a cyclic boron amide where said chain or ring contains from 2 to 20 carbon atoms and, optionally, 1–3 heteroatoms which can be N, S, or O,
 f) a cyclic boron amide-ester where said chain or ring contains from 2 to 20 carbon atoms and, optionally, 1–3 heteroatoms which can be N, S, or O;

n is 0 or 1;
p is 0 to 3;
r is 0 to 2;
s is 1 to 4; and
t is 1 to 3.

2. A compound of claim 1 where:

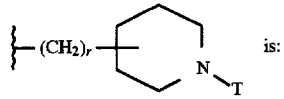 is:

a) 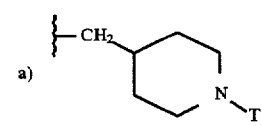

or b) 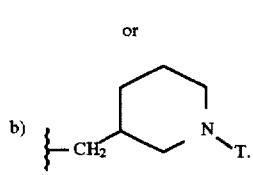

3. A pharmaceutical composition comprising a pharmaceutically suitable carrier and a therapeutically effective amount of a compound of claim 1.

4. A pharmaceutical composition comprising a pharmaceutically suitable carrier and a therapeutically effective amount of a compound of claim 2.

5. A method of treating thrombosis in a warm blooded animal by inhibition of trypsin-like serine proteases of the blood coagulation cascade, said method comprising administering to an animal in need of such treatment an effective amount of a compound of claim 1.

6. A method of treating thrombosis in a warm blooded animal by inhibition of trypsin-like serine proteases of the blood coagulation cascade, said method comprising administering to an animal in need of such treatment an effective amount of a compound of claim 2.

* * * * *

UNITED STATES PATENT AND TRADEMARK OFFICE
CERTIFICATE OF CORRECTION

PATENT NO : 5,731,439

DATED : March 24, 1998

INVENTOR(S) : David John Carini, et al.

It is certified that error appears in the above-identified patent and that said Letters Patent is hereby corrected as shown below:

On title page, item 54 Patent Title
 replace "AMINOBORNIC"
 with --AMINOBORONIC--.

Col. 1, line 1
 replace "AMINOBORNIC"
 with --AMINOBORONIC--.

Col. 7, line 5
 replace "carboxlic"
 with --carboxylic--.

Col. 7, line 56
 replace "DNA"
 with --pNA--.

Col. 7, line 63
 replace "DIBAI"
 with --DIBAL--.

Col. 8, line 65
 replace "flurines"
 with --fluorines--.

Col. 11, line 44
 replace "presense"
 with --presence--.

UNITED STATES PATENT AND TRADEMARK OFFICE
CERTIFICATE OF CORRECTION

PATENT NO. : 5,731,439
DATED : March 24, 1998
INVENTOR(S) : David John Carini, et. al.

It is certified that error appears in the above-indentified patent and that said Letters Patent is hereby corrected as shown below:

Col. 13, line 5
 replace "followed isobutyl"
 with --followed by isobutyl--.

Signed and Sealed this

Nineteenth Day of October, 1999

Q. TODD DICKINSON

Attest:

Attesting Officer

Acting Commissioner of Patents and Trademarks